United States Patent
Ozawa et al.

(10) Patent No.: US 8,652,199 B2
(45) Date of Patent: Feb. 18, 2014

(54) STENT WITH AUTONOMIC FUNCTION

(75) Inventors: Michihide Ozawa, Sendai (JP); Kiyoshi Yamauchi, Sendai (JP); Yuji Sutou, Sendai (JP); Takamitsu Takagi, Sendai (JP); Shuzou Yamashita, Okayama (JP); Kouji Mori, Okayama (JP)

(73) Assignees: NEC Tokin Corporation, Sendai-Shi (JP); Tohoku University, Sendai-Shi (JP); Japan Stent Technology Co., Ltd., Okayama-Shi (JP)

( * ) Notice: Subject to any disclaimer, the term of this patent is extended or adjusted under 35 U.S.C. 154(b) by 487 days.

(21) Appl. No.: 11/915,070

(22) PCT Filed: May 23, 2006

(86) PCT No.: PCT/JP2006/310197
§ 371 (c)(1),
(2), (4) Date: Feb. 5, 2008

(87) PCT Pub. No.: WO2006/126513
PCT Pub. Date: Nov. 30, 2006

(65) Prior Publication Data
US 2009/0062906 A1 Mar. 5, 2009

(30) Foreign Application Priority Data
May 23, 2005 (JP) .................... 2005-148995

(51) Int. Cl.
*A61F 2/06* (2013.01)
(52) U.S. Cl.
USPC ................. 623/1.19; 623/1.18; 623/1.15

(58) Field of Classification Search
USPC ............................. 623/1.15, 1.19
See application file for complete search history.

(56) References Cited

U.S. PATENT DOCUMENTS

| | | | |
|---|---|---|---|
| 3,174,851 A | 3/1965 | Buehler et al. | |
| 4,631,094 A | 12/1986 | Simpson et al. | |
| 4,770,725 A | 9/1988 | Simpson et al. | |
| 4,894,100 A | 1/1990 | Yamauchi et al. | |
| 5,441,515 A * | 8/1995 | Khosravi et al. | 606/194 |
| 5,601,593 A * | 2/1997 | Freitag | 623/1.19 |

(Continued)

FOREIGN PATENT DOCUMENTS

| | | |
|---|---|---|
| JP | 58-161753 A | 9/1983 |
| JP | 63-014834 A | 1/1988 |

(Continued)

OTHER PUBLICATIONS

D. Goldstein et al., "Nitinol-Based Fuze Arming Component", NSWC TR 88-340 (1988).

(Continued)

*Primary Examiner* — David Isabella
*Assistant Examiner* — Jacqueline Woznicki
(74) *Attorney, Agent, or Firm* — Holtz, Holtz, Goodman & Chick, PC

(57) ABSTRACT

To provide a stent which holds various performances such as deliverability, prevention of restenosis, flexible shape conformability, and so on and is therefore adaptable not only to a bile duct but also to a blood vessel system such as a tortuous coronary artery substantially without causing restenosis. A stent with an autonomic function is made of a Ti—Ni based shape memory alloy and has a maximum expanding force at a center portion in its lengthwise direction.

4 Claims, 2 Drawing Sheets

| | SECOND PART (END PORTION) | FIRST PART (CENTER PORTION) | SECOND PART (END PORTION) |
|---|---|---|---|
| HEAT TREATMENT: | AGING | SOLUTION TREATMENT | AGING |
| CHARACTERISTIC AT 37°C: | SHAPE MEMORY | SUPER-ELASTICITY | SHAPE MEMORY |

(56) References Cited

U.S. PATENT DOCUMENTS

| | | | |
|---|---|---|---|
| 5,618,299 A * | 4/1997 | Khosravi et al. | 623/1.2 |
| 5,667,522 A * | 9/1997 | Flomenblit et al. | 606/198 |
| 6,159,238 A * | 12/2000 | Killion et al. | 623/1.11 |
| 6,312,455 B2 | 11/2001 | Duerig et al. | |
| 6,375,458 B1 * | 4/2002 | Moorleghem et al. | 433/2 |
| 6,451,052 B1 * | 9/2002 | Burmeister et al. | 623/1.16 |
| 6,468,303 B1 * | 10/2002 | Amplatz et al. | 623/1.2 |
| 6,485,507 B1 * | 11/2002 | Walak et al. | 623/1.15 |
| 6,582,461 B1 | 6/2003 | Burmeister et al. | |
| 6,626,937 B1 * | 9/2003 | Cox | 623/1.18 |
| 6,652,576 B1 * | 11/2003 | Stalker | 623/1.18 |
| 6,719,781 B1 * | 4/2004 | Kim | 623/1.13 |
| 6,997,947 B2 * | 2/2006 | Walak et al. | 623/1.18 |
| 7,128,758 B2 * | 10/2006 | Cox | 623/1.19 |
| 7,244,319 B2 * | 7/2007 | Abrams et al. | 148/402 |
| 7,258,753 B2 * | 8/2007 | Abrams et al. | 148/402 |
| 7,632,303 B1 * | 12/2009 | Stalker et al. | 623/1.19 |
| 2001/0007953 A1 | 7/2001 | Duerig et al. | |
| 2002/0151966 A1 * | 10/2002 | Eder et al. | 623/1.18 |
| 2003/0109918 A1 * | 6/2003 | Walak et al. | 623/1.18 |
| 2004/0059410 A1 * | 3/2004 | Cox | 623/1.19 |
| 2004/0193257 A1 * | 9/2004 | Wu et al. | 623/1.46 |
| 2005/0096733 A1 | 5/2005 | Kovneristy et al. | |
| 2005/0209683 A1 * | 9/2005 | Yamauchi et al. | 623/1.15 |
| 2006/0086440 A1 * | 4/2006 | Boylan et al. | 148/563 |
| 2006/0100693 A1 * | 5/2006 | Walak et al. | 623/1.18 |
| 2007/0044868 A1 * | 3/2007 | Yamauchi et al. | 148/402 |
| 2009/0068054 A1 | 3/2009 | Ozawa et al. | |
| 2011/0152994 A1 * | 6/2011 | Hendriksen et al. | 623/1.11 |

FOREIGN PATENT DOCUMENTS

| | | |
|---|---|---|
| JP | 63-014835 A | 1/1988 |
| JP | 63-171844 A | 7/1988 |
| JP | 3-268749 A | 11/1991 |
| JP | 5-295498 A | 11/1993 |
| JP | 7-252553 A | 10/1995 |
| JP | 10-500595 A | 1/1998 |
| JP | 11-42283 A | 2/1999 |
| JP | 11-099207 A | 4/1999 |
| JP | 2003-102849 A | 4/2003 |
| JP | 2004-321348 A | 11/2004 |
| WO | WO 95/27092 A1 | 10/1995 |
| WO | WO 2004/017865 A1 | 3/2004 |

OTHER PUBLICATIONS

K. Otsuka et al., "Shape Memory Materials", 1998, Cambridge University Press, pp. 254-26.

T. Takagi et al., "Chodansei Ti—Ni—Nb Gokin no Gyakuhentai Kyodo ni Oyobosu Yowai Koka", The Japan Institute of Metals Koen Gaiyo, Vo.136, Mar. 29, 2005, p. 403.

M. Ozawa et al., "Ti—Ni-kei Keijo Kioku Gokin ni Okeru Reikan Kako ni Oyobosu Nb Tenkaryo to Hentai Ondo no Eikyo", Nippon Kikai Gakkai Zairyo Rikigaku Bumon Koenkai Koen Ronbunshu, vols. 507-508, 20.

M. Ozawa et al., "Ti—Ni—Nb Alloy Device", U.S. Appl. No. 11/915,130, filed Feb. 5, 2009.

Japanese Office Action dated Jan. 26, 2011 (and English translation of the relevant part thereof) in counterpart Japanese Application No. 2005-148995.

Japanese Office Action dated Sep. 28, 2011 (and English translation of relevant parts thereof) in counterpart Japanese Application No. 2005-148995.

Japanese Office Action dated May 30, 2012 and English translation thereof in counterpart Japanese Application No. 2005-148995.

* cited by examiner

| SECOND PART (END PORTION) | FIRST PART (CENTER PORTION) | SECOND PART (END PORTION) |
|---|---|---|

| HEAT TREATMENT: | AGING | SOLUTION TREATMENT | AGING |
|---|---|---|---|
| CHARACTERISTIC AT 37°C: | SHAPE MEMORY | SUPER-ELASTICITY | SHAPE MEMORY |

(a)

TREATMENT AT 400°C x 50hr.

| SECOND PART (END PORTION) | FIRST PART (CENTER PORTION) | SECOND PART (END PORTION) |
|---|---|---|
| | | |
| APPLIED STRESS: 1 5 % | 1 3 % | 1 5 % |
| CHARACTERISTIC AT 37°C: SHAPE MEMORY | SUPER-ELASTICITY | SHAPE MEMORY |

STENT WITH AUTONOMIC FUNCTION

TECHNICAL FIELD

This invention relates to a stent to be placed in a lumen of a human body or an animal.

BACKGROUND ART

As well known, a shape memory alloy, such as a Ti—Ni alloy, exhibits a remarkable shape memory effect in association with martensitic reverse transformation and exhibits spontaneous shape recovery and excellent spring characteristics (superelasticity) in a parent phase region after the reverse transformation from a martensite region. The superelasticity is observed in a number of shape memory alloys and, among others, is particularly remarkable in the Ti—Ni alloy and a Ti—Ni—X alloy (X=V, Cr, Co, Nb, or the like).

The shape memory effect of the Ti—Ni alloy is described in Patent Document 1. The superelasticity of the Ti—Ni alloy is described in Patent Document 2.

On the other hand, the shape memory effect and the superelasticity of the Ti—Ni—X alloy are described, for example, in Patent Documents 3 and 4 for a Ti—Ni—V alloy and in Patent Document 5 for a Ti—Ni—Nb alloy.

As compared with the Ti—Ni alloy, the Ti—Ni—Nb alloy used in this invention exhibits a characteristic that temperature hysteresis of stresses is increased by applying a stress. Therefore, the Ti—Ni—Nb alloy is put into practical use as a joint for reactor piping.

Stent treatment is a new technique rapidly put into use in recent years. The stent is a mesh-like metal tube to be placed in a living body in order to prevent renarrowing or restenosis of a narrow portion, such as a blood vessel, after it is expanded. The stent is reduced in diameter and received in an end portion of a catheter. After introduced into the narrow portion, the stent is released from the catheter and expanded to be attached to an inner wall of a lumen such as a blood vessel.

In case of PTCA (percutaneous transluminal coronary angioplasty), the stent is expanded following a blood vessel expanding operation by inflation of a balloon set on an inner wall for housing. The stent is called a balloon expandable stent and formed by the use of a metal such as stainless steel or tantalum.

On the other hand, in order to prevent rupture of an aneurysm which may result in a subarachnoid hemorrhage or the like, blood supply to the aneurysm is stopped. As one of such techniques, use is made of embolization in which a metal coil, such as a platinum coil, is implanted into the aneurysm so as to form a blood clot. However, it is pointed out that a part of the blood clot may possibly be released from the metal and carried by a bloodstream to a periphery to block a blood vessel. In order to avoid this, consideration is made about a covered stent technique in which the aneurysm is embolized by the use of a graft. In this case, simultaneously when the stent is released from the catheter, the stent is expanded by its own spring function to press the graft against a blood vessel wall. Such stent is called a self expandable stent. For the self expandable stent, a material having an excellent spring characteristic is desired.

The Ti—Ni shape memory alloy is characterized in that, at a temperature above a reverse transformation finish temperature (Af point) at which reverse transformation of the alloy starting from a reverse transformation start temperature (As point) is finished, the alloy which has been deformed under an external load is recovered into an original shape simultaneously when the external load is released and that recoverable deformation reaches about 7% in case of an elongation strain. Herein, the As point means a shape recovery start temperature while the Af point means a shape recovery finish temperature (shape recovery temperature). For use as the stent, a hoop-shaped stent is formed into a size slightly greater than the lumen where the stent is to be placed. The stent is reduced in diameter and mounted to the catheter. Simultaneously when the stent is released from the catheter, the stent is spontaneously recovered into its original diameter to be brought into tight contact with the lumen. Thus, the alloy has the Af point not lower than a living body temperature (around 37° C.). As well as the above-mentioned merits, such superelastic stent has several demerits, such as occurrence of damage in the blood vessel wall, a positioning error in placement, lack in deliverability, and so on due to its spontaneous shape recovery characteristic. Therefore, it is difficult to use the superelastic stent in a blood vessel system such as a coronary system.

The stent for PTCA is preferably made of a metal material having a low elastic limit, which hardly damages the blood vessel and is excellent in deliverability. However, there is left a problem that a pressing force (expanding force) against a lumen wall after expansion is weak. As means to solve the problem, a stent using a shape memory alloy is proposed. Patent Document 6 describes that a Ti—Ni—Nb alloy, which is a material similar to that used in this invention, is applied to a stent. This document describes that the stent made of a Ti—Ni—Nb shape memory alloy and having a low Young's modulus upon shape recovery and a high Young's modulus upon shape deformation under an external load is obtained when the ratio of stress on loading to the stress on unloading at the respective inflection points on a stress-strain curve in alloy deformation is at least about 2.5:1. This stent exhibits superelasticity at the living body temperature after it is released from the catheter but does not sufficiently solve the above-mentioned problem (arbitrariness in positioning) as required in PTCA.

In Patent Document 7, the present inventors have proposed a stent closely related to this invention. Specifically, proposal is made of the stent which exhibits no shape memory at the living body temperature during insertion into the living body and exhibits superelasticity after shape recovery by inflation of a balloon. In the embodiment, it is described that the stent made of a Ti—Ni alloy or a Ti—Ni—X alloy (X=Cr, V, Cu, Fe, Co, or the like) is subjected to strong deformation to thereby elevate a recovery temperature. However, this document does not refer to a graded function of the stent. Further, a strain is given only by strong deformation of a slotted stent received in the catheter. Depending upon a slot shape, a sufficient effect is not obtained. Patent Document 8 discloses a stent using a Ti—Ni alloy or a Ti—Ni—X alloy and proposes to partly change the stiffness of the material by heat treatment. Specifically, such change by heat treatment provides a series of superelastic portions having a relatively high stiffness and plastically deformable portions having a relatively low stiffness (in the description, portions where the superelasticity is destroyed) which are alternately arranged. Thus, this technique is different in gist and means intended by this invention.

The stent is required to have functions such as deliverability (accessibility to peripheral or distal parts), prevention of restenosis (strong expanding force after placement), and flexible shape conformability. Following recent increase in stent treatment cases, a problem of restenosis after placement of the stent is exposed.

For example, in case where the stent is placed at a tortuous coronary artery lesion, a restenotic lesion after placement tends to occur at opposite ends of the stent which are most susceptible to stimulation. In this event, re-placement of the stent or bypass surgery must be performed so that mental and physical burdens on a patient are extremely heavy. The deliverability (accessibility to peripheral parts) during operation is achieved by using a stainless steel material. The strong expanding force after placement is achieved by a conventional Ti—Ni—X alloy superelastic material. In order to achieve the flexible shape conformability (relaxation of stimulation to the restenotic lesion) after placement, it is proposed to weaken the expanding force of the stent to relax the stimulation to the lumen. However, this results in loss of an inherent function (reinforcement of the lumen) of the stent. Practically, a material-based approach is difficult. Therefore, at present, stent processing such as designing of a slot shape is relied upon as secondary means. However, various essential problems are left unsolved.

Patent Document 1: U.S. Pat. No. 3,174,851
Patent Document 2: JP S58-161753 A
Patent Document 3: JP S63-171844 A
Patent Document 4: JP S63-14834 A
Patent Document 5: U.S. Pat. No. 4,770,725
Patent Document 6: JP H11-42283 A
Patent Document 7: JP H11-99207 A
Patent Document 8: JP 2003-505194 A

DISCLOSURE OF THE INVENTION

Problem to be Solved by the Invention

It is therefore a technical object of this invention to provide a stent which holds various performances such as deliverability (accessibility to peripheral parts), prevention of restenosis (strong expanding force after placement), flexible shape conformability, and so on and is therefore adaptable not only to a bile duct but also to a blood vessel system such as a tortuous coronary artery substantially without causing restenosis.

Means to Solve the Problem

According to this invention, there is provided a stent made of a Ti—Ni based shape memory alloy as a material, the stent having at least one parent phase region and at least one martensite region or two or more parent phase regions different in shape recovery temperature arranged along its lengthwise direction so that a tensile strength in the lengthwise direction is varied. The stent holds a part or all of the above-mentioned performances by automatically adjusting a function during operation and placement.

The Ti—Ni based shape memory alloy used in this invention is a shape memory alloy containing titanium (Ti) and nickel (Ni) as essential components, for example, a Ti—Ni alloy or a Ti—Ni—X alloy (herein, X being an element such as Fe, V, Cr, Vo, Nb, or the like).

In this invention, by providing the martensite region occupying ⅔ or more (preferably ⅘ or more) of the total length, it is possible to provide a stent which is, as a stent function during operation, excellent in operability and suppressed in risk of damaging a lumen wall due to spontaneous shape recovery. Further, by providing the parent phase region at the center portion in the lengthwise direction, it is possible to provide a stent which is, as a stent function during placement, excellent in expanding force.

Further, in this invention, by providing the parent phase region at the center portion of the lengthwise direction and, at opposite ends, the martensite regions or the parent phase regions smaller in expanding force than the center portion, it is possible to provide a stent excellent in shape conformability.

Effect of the Invention

According to this invention, it is possible to provide a stent which hardly causes a restenosis lesion not only in a blood vessel of a human body or an animal but also in various kinds of lumens and which is readily operable.

BRIEF DESCRIPTION OF THE DRAWING

FIG. 3 A photograph showing, as one example of characteristic impartment, a metallographic structure of the stent with an autonomic function according to this invention in case where a strain is applied after slotting a pipe.

BEST MODE FOR EMBODYING THE INVENTION

Now, an embodiment of this invention will be described. In the following description, an alloy wire rod or simply a wire rod refers to an alloy material or a material in the form of a hollow thin wire.

(a) At first, a heat-treatment effect will be described.

Figure 1:
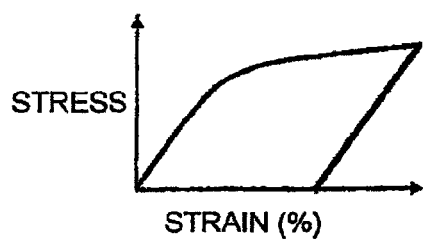
FIG. 1 A photograph showing a metallographic structure of a stent with an autonomic function according to this invention in case where a heavily deformed Ti-51 at % Ni alloy tube is laser-machined, expanded, and imparted or assigned with characteristics.

By high-frequency melting, hot working, and cold working, a hollow wire rod was obtained which was made of a Ti-51 at % Ni alloy, formed into a tube having an outer diameter of ø2 mm and a thickness of 0.15 mm, and reduced in diameter to ø1 mm. The tube was subjected to laser machining and thereafter expanded into ø5 mm to obtain a stent illustrated in FIG. 1. In the following description, an alloy wire rod or simply a wire rod refers to an alloy material or a material in the form of a hollow thin wire.

Next, the stent was, over its entire length, subjected to aging at 400° C. for 50 hours. Thereafter, one sample was, only at the center of the stent, subjected to heat treatment again at 500° C. for 5 minutes. Another sample was similarly subjected to heat treatment again at 700° C. for 0.5 minute.

Figure 2:
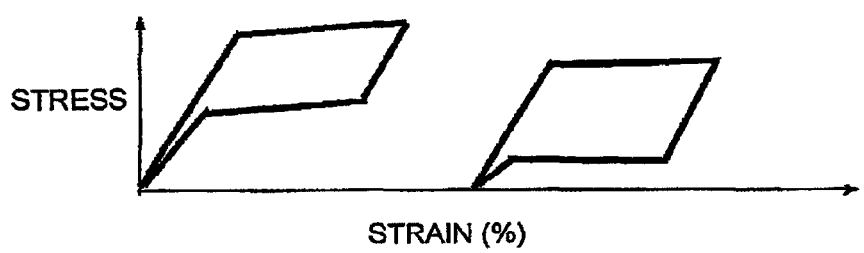
FIG. 2 A stress-strain curve for the stent with an autonomic function according to this invention in case where a heavily deformed Ti-51 at % Ni alloy wire is heat treated at 400° C., 500° C., and 700° C.

FIGS. 2(a) and (b) show stress-strain curves at 37° C. for heat-treated test samples of the above-mentioned wire rods having a diameter of ø1 mm. It is understood that the aged material in FIG. 2(a) heat treated at 400° C. for 50 hours (hereinafter called a 400° C. aged material) has a martensite region. In (b), the material heat treated at 500° C. for 5 minutes (hereinafter called a 500° C. heat-treated material) and the material heat-treated at 700° C. for 0.5 minute (hereinafter called a 700° C. heat-treated material) have parent phase regions.

The shape recovery temperature of the stent using the tube is obtained by reducing the diameter into ø2 mm in a dry ice alcohol bath (at about −50° C.) and then gradually heating the stent. It has been confirmed that characteristics of respective portions at 37° C. are similar to those in (a) and (b) of FIG. 2.

The amount of self recovery of the center portion of the stent after it is released from a catheter can be selected by the length of the parent phase region in the length of the stent and the strength of recovery. In this example, with the treatment at 500° C., self recovery of the center portion of the stent was observed in case where the parent phase region was shorter than ⅘ of the stent length. However, with the treatment at 700° C., the recovery of the center portion could be suppressed when the parent phase region was shorter than ⅔ of the stent length. The opposite end portions as the martensite regions and the unrecovered center portion were recovered into the original stent shape by balloon expansion. From the above, it has been revealed that, by selecting heat-treatment conditions and heat-treatment zones, necessity or unnecessity of balloon expansion at the living body temperature and the change in tensile strength after placement in the stent length direction can be achieved as desired.

It is known that the change in transformation temperature of the alloy is obtained by appearance of an R phase caused by aging in case of an Ni-excess Ti—Ni alloy and a Ti—Ni—X alloy with Fe, V, Co, Cr, Nb, or the like added and obtained by aging after strong deformation (thermomechanical treatment) in case of all kinds of Ti—Ni alloy and the Ti—Ni—X alloy exhibiting a shape memory effect. A superelastic recovering force in the parent phase region is obtained as ΔT (=measurement temperature−Af temperature) is greater and the density of deformation texture in the alloy is higher. In this case also, functionality was considered about various kinds of alloys such as a Ti-50 at % Ni alloy, a Ti-49 at % Ni-1 at % V alloy, and a Ti-48 at % Ni-3 at % Nb alloy. As a result, by appropriately selecting the working conditions and the heat-treatment conditions, the effect of this invention could be obtained. For example, in case of the Ti-50 at % Ni alloy, a slotted tube having a diameter of ø2 mm is expanded into ø5 mm by strong deformation. Thereafter, only opposite end portions are heated at 600° C. in a short time (1 to 2 seconds). Thus, the stent is obtained which is superelastic at the center portion (parent phase region) and which has the martensite regions at the opposite end portions and is different in function in the lengthwise direction.

(b) Next, a prestrain effect will be described.

As shown by Nos. 1, 2, and 3 in Table 1, wire rods made of Ti-51 at % Ni, Ti-49 at % Ni-3 at % Nb, and Ti-47.5 at % Ni-6 at % Nb alloys and having a diameter of ø1 mm with a cold working rate of 30% were heat-treated at 400° C. for one hour. The relationship between the applied strain (applied at a temperature not higher than the As point) and the shape recovery temperature was examined for each sample. The result is shown in Table 1 also.

The alloy No. 1 shown in Table 1 had a shape recovery temperature of 20° C. at a strain ($\epsilon$)=0%, a shape recovery temperature of 20° C. at $\epsilon$=8%, a shape recovery temperature of 25° C. at $\epsilon$=10%, a shape recovery temperature of 30° C. at $\epsilon$=13%, and a shape recovery temperature of 30° C. at $\epsilon$=15%.

The alloy No. 2 had a shape recovery temperature of 10° C. at $\epsilon$=0%, a shape recovery temperature of 12° C. at $\epsilon$=8%, a shape recovery temperature of 25° C. at $\epsilon$=13%, and a shape recovery temperature of 30° C. at $\epsilon$=15%.

The alloy No. 3 had a shape recovery temperature of 18° C. at $\epsilon$=0%, a shape recovery temperature of 23° C. at $\epsilon$=8%, a shape recovery temperature of 28° C. at $\epsilon$=10%, and a shape recovery temperature of 50° C. at $\epsilon$=15%.

In each of the alloys Nos. 1, 2, and 3, an increase in shape recovery temperature by prestrain is observed. In particular, this effect is remarkable in the 6 at % Nb-added alloy as the sample No. 3. It has been found out that, by adjusting the applied strain, the stent function can be changed in the lengthwise direction. For example, the applied strain is 10% at the center portion of the stent and 13% at the opposite end portions, the shape recovery temperature of the stent exceeds the living body temperature. Therefore, the deliverability during operation is assured. By heating (at 42° C.) after placement, the entire length of the stent is transformed into the parent phase region and the expanding force at the center portion can be increased. Alternatively, it is possible to provide a stent in which only the end portions are applied with the strain of 13% or more to be transformed into the martensite regions. Further, in the sample No. 1 alloy and the sample No. 2 alloy also, the shape recovery temperature during heat treatment is controlled by aging or thermomechanical treatment so that the change in stent function by prestrain can be made like in the sample No. 3 alloy. Thus, the effect of this invention can be obtained.

FIG. 3 shows, as one example of characteristic impartment, the stent with an autonomic function according to this invention in case where a strain is applied after slotting a pipe.

Next, a tapered wedge was inserted into a slotted tube of the Ti-46.5 at % Ni-6 at % Nb alloy as the sample No. 3 having a diameter of ø2 mm. As shown in FIG. 3, the opposite end portions were applied with a strain of 15% and the center portion was applied with a strain of 13%. Heat treatment was carried out at 400° C. for one hour. Thereafter, the stent was reduced in diameter into ø2.0 mm and a prestrain was applied. Then, the stent was mounted to a catheter. After released from the catheter, shape recovery of the stent was similar to that in the test result for the wire. The functionality changed in the lengthwise direction was confirmed.

TABLE 1

| | Composition (at %) | | | shape recovery temperature (° C.) | | | | |
|---|---|---|---|---|---|---|---|---|
| No. | Ti | Ni | Nb | $\epsilon$ = 0% | $\epsilon$ = 8% | $\epsilon$ = 10% | $\epsilon$ = 13% | $\epsilon$ = 15% |
| 1 | 49 | 51 | 0 | 20 | 20 | 25 | 30 | 30 |
| 2 | 49 | 48 | 3 | 10 | 12 | 15 | 25 | 30 |
| 3 | 47.5 | 46.5 | 6 | 18 | 23 | 28 | 42 | 50 |

(c) Next, the heat treatment and the prestrain effect will be described.

The Ti—Ni shape memory alloy has a yield stress depending upon the temperature. In the superelasticity at the living body temperature also, the yield stress is higher and the expanding force is greater as the shape recovery temperature is lower. In this example, by the use of the sample No. 3 alloy mentioned above, the stent was prepared under the conditions shown in Table 2. Specifically, the entire length of the stent was heat treated at 400° C. Thereafter, the opposite end portions alone were heat treated at about 525° C. Thereafter, in the above-mentioned manner, required strains $\epsilon$=13% and $\epsilon$=8% were applied. After heating to 42° C., the stent function was examined. As a result, the change in expanding force at 37° C. was observed.

TABLE 2

| | composition (at %) | | | heat treatment | Af (° C.) at $\epsilon$ = 0% | required strain to Af = 42° C. |
|---|---|---|---|---|---|---|
| No. | Ti | Ni | Nb | | | |
| 3 | 47.5 | 46.5 | 6 | 400° C., 1 hr | 15 | $\epsilon$ = 13% |
| | | | | 525° C., 1 min | 35 | $\epsilon$ = 8% |

(d) Next, the applicability will be described.

Herein, the operability of the stent was verified by the use of a swine blood vessel. The stent exhibiting a shape recovery temperature higher than 37° C. as an example of this invention exhibited smooth deliverability for the tortuous blood vessel and arbitrariness of placement to lesions. Physiologic saline for use in a balloon expanding operation after placement was kept at 45° C. and used to heat the stent. As a result, the stent holds desired functions (having the martensite region partially and the parent phase region partially, or entirely having the parent phase region with variation in expanding force).

As described above, according to this invention, desired stent characteristics depending upon the condition of the lesions can be achieved by material design although this approach have been difficult so far. It is possible to achieve a new design of the stent.

Alloys applicable to this invention include a Ti—Ni based alloy exhibiting a shape memory effect and a Ti—Ni—X alloy containing third and fourth elements such as Fe, Cr, V, Co, Nb and so on.

A suitable alloy in this invention using the heat treatment effect is an Ni-excess alloy, such as a Ti-51 at % Ni alloy, easy in appearance of an R phase by aging. A suitable alloy using the prestrain effect is a Ti—Ni—Nb alloy and the content of Nb is 3 at % or more exhibiting a remarkable effect of addition. Excessive addition degrades workability of the alloy. Preferably, the content is 6 to 9 at %.

INDUSTRIAL APPLICABILITY

As described above, the stent according to this invention is most suitable as a stent with an autonomic function excellent in deliverability, expanding force, and shape conformability and autonomously adaptable to lesions in a living lumen.

The invention claimed is:

1. A stent having an autonomic function, comprising a Ti—Ni based shape memory alloy of a thin long cylindrical shape or a wire shape,
wherein the stent has a first part and a second part that is different from the first part in a lengthwise direction,
wherein the first part comprises a center portion of the stent in the lengthwise direction and the second part comprises two end portions of the stent outside the first part,
wherein the stent has a parent phase region at the first part and a martensite region at the two end portions of the second part before or at a time of placement of the stent in a lumen,
wherein the stent has been subjected to different processes by which different strains are applied at the first part and at the second part,
wherein the stent has a maximum expanding force at the first part which depends on a state of phase or a shape recovery temperature at the first part, and
wherein each of the center portion and the two end portions are subjected to a shape memory treatment so that the stent has the thin cylindrical shape or the wire shape in which the two end portions and the center portion have identical diameters after balloon expansion.

2. The stent having an autonomic function according to claim 1, wherein the stent is made of a Ti—Ni alloy or a Ti—Ni—X alloy where X is at least one element selected from Fe, V, Cr, Co, and Nb.

3. The stent having an autonomic function according to claim 1, wherein the Ti—Ni based shape memory alloy is a Ti-47.5-51 at % Ni-0-9 at % Nb alloy.

4. The stent having an autonomic function according to claim 1, wherein the Ti—Ni based shape memory alloy is formed into one body and has a same composition at any part along the lengthwise direction.

* * * * *